United States Patent
Ver Steeg et al.

(10) Patent No.: US 12,213,807 B2
(45) Date of Patent: Feb. 4, 2025

(54) SYSTEM AND METHOD FOR POSITIONING A SENSOR ON A SUBJECT

(71) Applicant: ROCKLEY PHOTONICS LIMITED, Altrincham (GB)

(72) Inventors: Benjamin Ver Steeg, Redlands, CA (US); Amit Singh Nagra, Altadena, CA (US); Haydn Frederick Jones, London (GB)

(73) Assignee: Rockley Photonics Limited, Altrincham (GB)

( * ) Notice: Subject to any disclaimer, the term of this patent is extended or adjusted under 35 U.S.C. 154(b) by 0 days.

(21) Appl. No.: 17/817,321

(22) Filed: Aug. 3, 2022

(65) Prior Publication Data

US 2023/0038906 A1     Feb. 9, 2023

Related U.S. Application Data

(60) Provisional application No. 63/230,590, filed on Aug. 6, 2021.

(51) Int. Cl.
*A61B 5/00*     (2006.01)
*A61B 5/024*     (2006.01)

(52) U.S. Cl.
CPC .......... *A61B 5/6835* (2013.01); *A61B 5/0075* (2013.01); *A61B 5/02416* (2013.01); *A61B 5/6833* (2013.01); *A61B 5/7235* (2013.01); *A61B 5/7278* (2013.01)

(58) Field of Classification Search
None
See application file for complete search history.

(56) References Cited

U.S. PATENT DOCUMENTS

| | | | |
|---|---|---|---|
| 11,375,941 B2 | 7/2022 | Szabados et al. | |
| 2003/0069484 A1 | 4/2003 | Blank et al. | |
| 2008/0146899 A1 | 6/2008 | Ruchti et al. | |
| 2009/0318793 A1* | 12/2009 | Datta | A61B 5/06 600/391 |
| 2010/0210946 A1* | 8/2010 | Harada | A61B 8/4281 600/443 |
| 2016/0089041 A1* | 3/2016 | Keat | G06T 7/246 600/479 |
| 2018/0193098 A1* | 7/2018 | Caluser | A61B 5/164 |
| 2018/0235532 A1 | 8/2018 | Newberry | |
| 2019/0053784 A1* | 2/2019 | Beri | A61B 8/4218 |
| 2020/0223805 A1* | 7/2020 | Le | A61B 5/201 |
| 2020/0305798 A1 | 10/2020 | Ishikawa et al. | |
| 2020/0330068 A1* | 10/2020 | Mudge | A61B 5/6833 |
| 2021/0267572 A1* | 9/2021 | Sutton | A61B 8/4209 |

(Continued)

OTHER PUBLICATIONS

International Search Report and Written Opinion of the International Search Authority, mailed Nov. 25, 2022, corresponding to PCT/EP2022/072094, 17 pages.

(Continued)

*Primary Examiner* — Shahdeep Mohammed
(74) *Attorney, Agent, or Firm* — Lewis Roca Rothgerber Christie LLP

(57) ABSTRACT

A system and method for positioning a sensor on a subject. In some embodiments, the system includes an instrument holder, the instrument holder being configured to be secured to a subject, and to hold an instrument temporarily.

9 Claims, 2 Drawing Sheets

(56) References Cited

U.S. PATENT DOCUMENTS

2022/0153708 A1* 5/2022 Le .......................... A61B 5/201

OTHER PUBLICATIONS

Mohamed, E., Abstract of "Optimal Signal Quality Index for Photoplethysmogram Signals", Database Medline [Online] U.S. National Library of Medicine, Sep. 22, 2016, vol. 3, No. 4, Database accession No. NLM28952584, ISSN: 2306-5354, Bioengineering (Basel, Switzerland).

* cited by examiner

SYSTEM AND METHOD FOR POSITIONING A SENSOR ON A SUBJECT

CROSS-REFERENCE TO RELATED APPLICATION(S)

The present application claims priority to and the benefit of U.S. Provisional Application No. 63/230,590, filed Aug. 6, 2021, entitled "SYSTEM AND METHOD FOR SENSING BIOMARKERS", the entire content of which is incorporated herein by reference.

FIELD

One or more aspects of embodiments according to the present disclosure relate to sensing, and more particularly to a system and method for positioning a sensor on a subject.

BACKGROUND

When performing medical or health-related measurements, diagnostics or assessments of a subject (e.g., a patient) an instrument or other sensor may be positioned on the subject for the purpose or making measurements, e.g., of biomarkers (such as glucose, alcohol, or water) in the tissue of the subject. The quality of the measurements may depend on the positioning of the instrument on the subject. Moreover, if the instrument is removed from the subject and later placed on the subject again, the extent to which new measurements are comparable to previously made measurements may depend on the extent to which the new position of the instrument is the same as the previous position.

It is with respect to this general technical environment that aspects of the present disclosure are related.

SUMMARY

According to an embodiment of the present disclosure, there is provided a system, including: an instrument holder, the instrument holder being configured to be secured to a subject, and to hold an instrument temporarily.

In some embodiments, the instrument holder is configured to hold the instrument in a position, relative to the instrument holder, that is repeatable to within 2 mm along each of three orthogonal directions, and within 5 degrees for rotation about each of the three orthogonal directions.

In some embodiments, the instrument holder is secured to the subject by an adhesive.

In some embodiments, the instrument holder includes a fabric portion, secured to the subject by the adhesive, and a rigid portion secured to the fabric portion.

In some embodiments, the instrument holder includes a detent to hold the instrument.

In some embodiments, the detent includes a protrusion or a recess, configured to engage a recess or a protrusion of the instrument.

In some embodiments, the instrument holder includes a wall having a rib configured to engage a groove in a corresponding wall of the instrument, and the detent includes the rib.

In some embodiments, the instrument holder includes one or more walls surrounding a volume for accommodating the instrument.

In some embodiments, the system further includes a cap configured to be installed in the volume in place of the instrument.

In some embodiments, the cap has a porous top.

In some embodiments, the system further includes the instrument, wherein the instrument includes a spectrophotometer.

In some embodiments, the instrument further includes a photoplethysmography sensor.

According to an embodiment of the present disclosure, there is provided a method for positioning an instrument, the method including: holding, by an instrument holder, the instrument on a first occasion; and holding, by the instrument holder, the instrument on a second occasion, wherein: the instrument includes a sensor.

In some embodiments, the method further includes calculating a repeatability metric based on a measurement obtained by the sensor on the first occasion and a measurement obtained by the sensor on the second occasion.

In some embodiments, the calculating of the repeatability metric includes calculating a difference between a peak-to-trough measurement obtained on the first occasion and a peak-to-trough measurement obtained on the second occasion, each of the peak-to-trough measurements being a difference between a maximum measured value and a minimum measured value.

In some embodiments: the sensor includes a spectrophotometer, and the peak-to-trough measurement obtained on the first occasion is the difference between: a maximum reading, over wavelength, obtained by the spectrophotometer, and a minimum reading, over wavelength, obtained by the spectrophotometer.

In some embodiments: the sensor includes a spectrophotometer; the measurement obtained by the sensor on the first occasion includes a first vector of spectral samples; the measurement obtained by the sensor on the second occasion includes a second vector of spectral samples; the calculating of the repeatability metric includes calculating a distance between a first vector of scalar projections and a second vector of scalar projections; each element of the first vector of scalar projections is a scalar projection of the first vector of spectral samples onto a corresponding loading vector of a plurality of loading vectors; and each element of the second vector of scalar projections is a scalar projection of the second vector of spectral samples onto a corresponding loading vector of the plurality of loading vectors.

In some embodiments, the distance is a Mahalanobis distance.

In some embodiments, the distance is a Euclidean distance.

BRIEF DESCRIPTION OF THE DRAWINGS

These and other features and advantages of the present disclosure will be appreciated and understood with reference to the specification, claims, and appended drawings wherein:

DETAILED DESCRIPTION

Figure 1A:
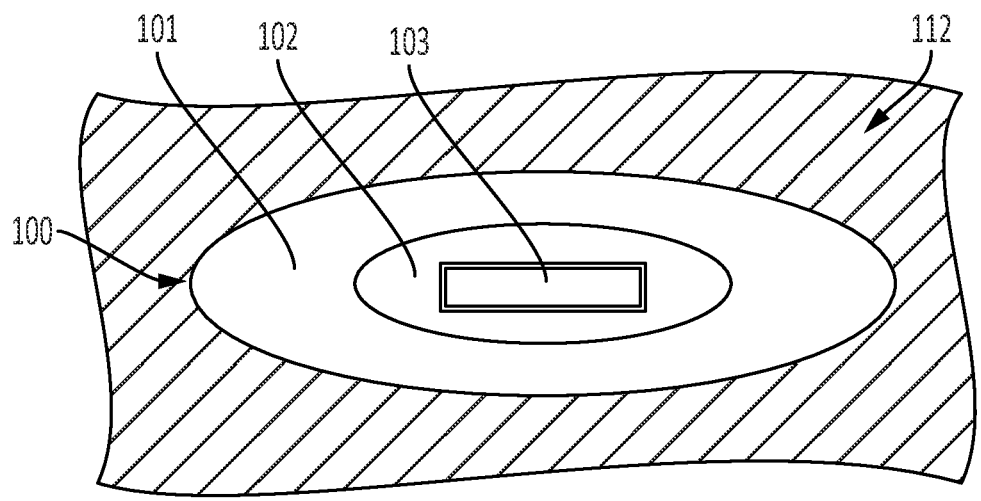
FIG. 1A is a top view of an instrument holder, according to an embodiment of the present disclosure.

The detailed description set forth below in connection with the appended drawings is intended as a description of exemplary embodiments of a system and method for positioning a sensor on a subject provided in accordance with the present disclosure and is not intended to represent the only forms in which the present disclosure may be constructed or utilized. The description sets forth the features of the present disclosure in connection with the illustrated embodiments. It is to be understood, however, that the same or equivalent functions and structures may be accomplished by different embodiments that are also intended to be encompassed within the scope of the disclosure. As denoted elsewhere herein, like element numbers are intended to indicate like elements or features.

Non-invasive sensing of biomarkers through the skin by means of spectroscopy, e.g., spectrophotometry, is developing rapidly in terms of selectivity and sensitivity. In other words, more analytes can be detected and measured at lower concentrations by through-skin spectroscopy of various sorts. In some embodiments, a wearable or portable device is used to perform in vivo optical measurements on a user, e.g., a patient or a "subject". For example, a point on the user's skin may be illuminated with an optical probe beam, and the intensity or irradiance of scattered or transmitted light (which may exit the skin at another point) may be measured as a function of wavelength. The probe light may be laser light and the laser light may be tunable in wavelength or may be of a number of fixed wavelengths switched on and off in sequence. From measurements of the scattered or transmitted light, the presence or concentrations of certain chemical compounds, in tissue within or beneath the user's skin, may be inferred. Similar methods may be used to analyze in vitro samples, such as whole blood. The wavelength range of the irradiating light may be visible, infra-red (IR), short-wave infra-red (SWIR), etc.

As sensitivity improves, variations in parameters such as absorbance become more affected by local variations in the tissue being interrogated. For example, the presence of blood vessels, lipid deposits, cartilage and so on varies—biological tissue is inhomogeneous on the macro scale. Thus, it may be advantageous for certain through-skin measurements to ensure that the transmitted light is applied to the skin time after time at the same spot and the receiver also is positioned at a respective, unchanging, spot. A watch-type fitting may move around on the wrist and as a result, if a spectrophotometer is installed in a watch or in another kind of module that is strapped to the subject's wrist, the emitted and received light may pass through different tissue regions as the watch or module moves across the skin. As such, in such a system, various methods may be used to ensure that a measurement is sufficiently analogous to a previously made measurement that a comparison between the measurements is meaningful.

A spectrophotometer may have one or more transmitting ports, at which the probe light is emitted, and one or more receiving ports, at which light may be received by the spectrophotometer after being transmitted through tissue of the subject (for example, after entering through the surface of the skin of the subject, propagating through tissue below the surface of the skin, and exiting the skin again). Because light may scatter within the tissue, the path of the light within the subject need not be straight, and, for example, light may enter at a first point on the top of the wrist, scatter within tissues under the surface of the skin, and exit at a second point on the top of the wrist.

In some embodiments, a patch with one or more apertures may be secured (e.g., by an adhesive adhering to the skin of the subject) to the subject (e.g., on the top of the wrist). The patch may, for example, have a first aperture corresponding to a transmitting port of the spectrophotometer and a second aperture corresponding to a receiving port of the spectrophotometer. In use, the user may be instructed to move the spectrophotometer relative to the patch until the transmitting port of the spectrophotometer (which may be secured (like a watch, or in a watch) to the wrist by a strap) is aligned with the first aperture and the receiving port of the spectrophotometer is aligned with the second aperture (as measured, for example, by the optical throughput (or "transmission") from the transmitter of the spectrophotometer to the receiver of the spectrophotometer).

Real-time feedback may be given to the user during this process, e.g., in the form of an audible tone (the frequency of which may increase, for example, with increasing optical throughput) or in the form of a graphical display indicating (e.g., by color, or intensity, or a needle or bar graph) the optical throughput. Once the spectrophotometer is adequately aligned, the user may hold it steady while one or more spectrophotometric measurements are made. In some embodiments, the patch may also serve the function of reducing the reception, by the receiver, of stray light and of light received from the transmitter without transmission through the tissue of the subject (e.g., light received after reflection from the surface of the skin of the subject). The patch may be designed to allow easy mechanical alignment with the sensor. For example, in some embodiments, alignment marks on the patch and on the spectrophotometer may help the user position the spectrophotometer in an initial position at which the optical throughput is sufficiently great to be measurable.

Figure 1B:
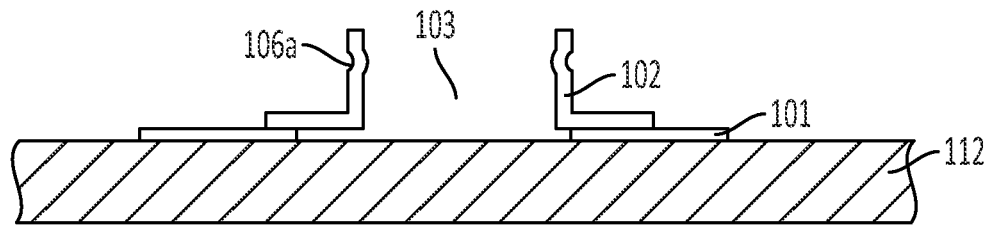
FIG. 1B is a schematic cross-sectional view of an instrument holder, according to an embodiment of the present disclosure.
Figure 1C:
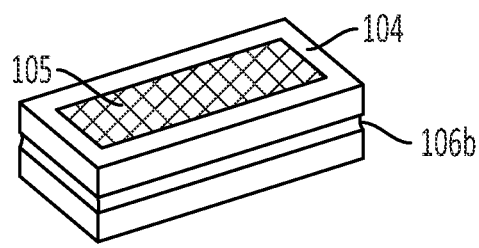
FIG. 1C is a perspective view of a cap, according to an embodiment of the present disclosure.

In another embodiment, referring to FIGS. 1A, 1B and 1C, a holder 100, (e.g., a spectrophotometer holder or, more generally, a sensor holder or an instrument holder), for holding the spectrophotometer at a certain, repeatable position, may be secured to the user (e.g., to the skin 112 of the user). A sensor module (which may include a spectrophotometer) may be temporarily placed on or in the holder 100 (e.g., the holder 100 may hold the sensor module temporarily) when measurements are to be made.

The holder 100 may include a flexible portion 101 (e.g., a patch of fabric with an adhesive coating) which may be adhered to the skin 112 of the subject. The material of the flexible portion 101 may be similar to an adhesive bandage, or "sticking plaster", and it and the whole holder 100 may be for one-time use. The holder 100 may also include a rigid portion 102 (e.g., a rigid polymer portion), secured to the flexible portion 101, for securing, or mounting, the sensor module. The rigid portion 102 may include, for example, an integral socket with an aperture 103, the material of the socket being made of sufficiently stiff material that a snap fitting can be made with a cap, or "cover", 104 or with the sensor module 107. A detent may be formed by a protrusion or a recess on the holder 100 that is configured to engage a corresponding recess or protrusion on the sensor module 107. For example, in FIGS. 1B-1E, a rib 106a on the holder 100 engages a corresponding groove 106b on the sensor module 107, to secure it in position when being held by the holder 100. The drawings show an oblong socket; in some embodiments, it may be oval, circular, or another shape. Referring to FIG. 1C, when the socket is not in use and holding the sensor module 107, a snap fit cover 104 may be installed in the socket. This cover 104 may have a porous top 105 in order that the skin within the patch can breathe.

Figure 1D:
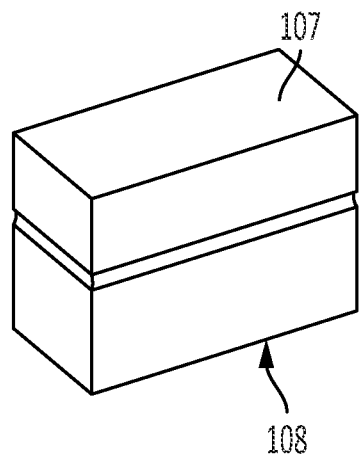
FIG. 1D is a perspective view of an instrument, according to an embodiment of the present disclosure.
Figure 1E:
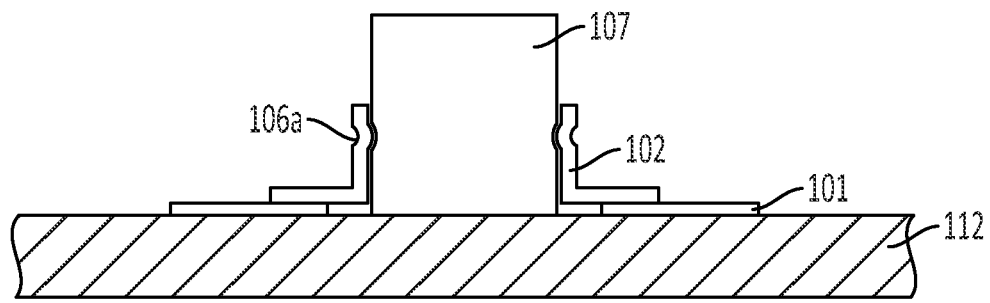
FIG. 1E is a schematic cross-sectional view of an instrument holder holding an instrument, according to an embodiment of the present disclosure.
Figure 1F:
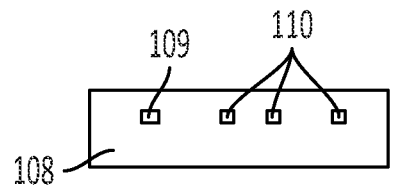
FIG. 1F is a bottom view of a spectrophotometer, according to an embodiment of the present disclosure.

FIG. 1D shows schematically a sensor module of some embodiments and FIG. 1F shows an example of the bottom face 108 of the sensor module, which contacts the skin. The bottom face 108 may have at least one optical transmitting aperture 109 and one or more receiving apertures 110. The sensor module 107 and the cover 104 may be of one of various shapes and the horizontal cross section may match the cross section of the aperture 103. FIG. 1E shows a sensor module or device 107 in the socket, engaged with the snap fitting and in contact (through surface 108) with the skin 112. The module 107 may be connected to its driver and host wirelessly (e.g. by Bluetooth) or by wire. If by wire, the sensor module 107 may have a plug/socket connection (not shown) to a cable.

The system illustrated in FIGS. 1A-1F may minimize errors (e.g., positioning errors) caused by removal and replacement of the sensor for purposes such as recharging or bathing. In some embodiments, when the sensor module 107 is removed from the holder and then returned to the holder, the new position of the sensor module 107 may differ from the previous position of the sensor module 107, relative to the holder, by a small amount in translation, or in rotation, or both. For example, a set of coordinate axes may be defined in which the x and y axes are parallel to the skin (and, e.g., for a rectangular socket, x is parallel to the longer side of the socket) and z is perpendicular to the skin. Then the difference between any installation position and a nominal, or ideal position may be described (i) in terms of the translational offset, along each of the three axes, between the installation position and the nominal position, and (ii) in terms of the rotational offset, about each of the three axes, between the installation position and the nominal position. If the maximum amount by which the sensor is capable of being displaced, in translation, from the nominal position is 1 mm along each of the axes, then the position of the sensor in the holder may be said to be repeatable to within 2 mm along each of three orthogonal directions (the orthogonal directions being, e.g., the axes; for example, on one occasion it may be installed with an offset, along the x axis, of 1 mm, and on another occasion it may be installed with an offset, along the x axis, of −1 mm, so that the two positions differ by 2 mm along the x axis). Similarly, if the maximum amount by which the sensor is capable of being displaced, in rotation, about each of the three axes, from the nominal position, is 2.5 degrees, then the position of the sensor in the holder may be said to be repeatable to within 5 degrees for rotation about each of the three orthogonal directions. For example, a subject may be fitted with multiple holders 100, and a sensor module 107 may be plugged into each in turn. As another example, it may be convenient to remove the sensor module 107 when the subject is to be repositioned (e.g., in a hospital bed) and then to plug it in again.

In some embodiments the holder 100 may have a different mechanical configuration while serving the same function of making it possible to remove the sensor module 107 and then to re-install the sensor module 107 at substantially the same position on the subject. For example, the holder 100 may be substantially flat except for several (e.g., three) snaps that may protrude from its surface to engage with corresponding snaps on the lower surface of, or on a flange around, the sensor module 107. In such an embodiment, the sockets for the snaps may be on the holder 100 and the balls, or buttons that engage with the sockets may protrude from a surface of (e.g., of a flange on) the spectrophotometer. These attachment points may be configured to include kinematic repositioning elements to reduce issues from mechanical overconstraint. Examples may include a combination of fixed attachment points and flexible attachment points in order to minimize repositioning error.

In some embodiments, instead of using a holder 100 or patch adhered to the skin of the subject, a camera may be used to achieve repeatable positioning of a spectrophotometer (or other instrument). The camera may be separate from the spectrophotometer, e.g., set up on a surface or on a tripod so that the portion of the subject's body (e.g., the subject's arm), where the spectrophotometer is to be placed, is within its field of view. Feedback may be provided to the user placing the spectrophotometer (e.g., to the subject, or to a healthcare worker placing the spectrophotometer on the subject) regarding adjustments needed in the position of the spectrophotometer. Such feedback may be provided via optical cursors (e.g., marks, superimposed on the camera's image of the subject's arm, identifying the target location for the spectrophotometer) or spots or beams projected onto the subject's arm, for example. In such an embodiment, the camera system may correct for any parallax errors, to account for offset between the displayed image and the sensing window. Haptic or other (e.g., audible) feedback may be provided to the user in addition to or instead of graphical feedback on a display, to guide the user, and, e.g., to alert the user (e.g., with a tone or with vibration of the spectrophotometer) when the spectrophotometer is correctly positioned. Voice feedback may also explicitly tell the user how to move or position the spectrophotometer.

In some embodiments, in addition to measuring, at each wavelength generated by the spectrophotometer, the transmission from the transmitter to the receiver (which may be related to absorbance, at that wavelength, of the tissues through which the light travels), the slope of the transmission with respect to wavelength may also be measured. In such an embodiment, some of the wavelengths of the spectrophotometer may be selected to be wavelengths at which the substances to be detected have different absorbances, and some may be selected to be wavelengths at which the absorbances of the substances to be detected have different slopes.

The measuring of the slopes may be performed using active scanning. For example each of the wavelengths at which the slope is to be measured may be dithered, and the extent to which the measured transmission (from transmitter to receiver) changes at the same frequency and with the same phase as the dither may be used to infer the slope. The optical power and the magnitude of the dither may be selected to provide acceptable signal to noise ratio in the measurement of the slope. Both the measured transmission (which may be related to the absorption and reflectance of the tissue of the subject) and slope (the rate of change of transmission with wavelength) may be used to fit to known substances that are being detected. In some embodiments, artificial intelligence (AI) and machine learning (ML) are used to train spectra for known blends or doing a gold standard measurement for the sample, in addition to the technique of measuring both absolute levels and local slopes. A sufficiently large training set may be used to obtain accurate results.

In some embodiments, measurements from the sensor may be used to position the sensor, or to reposition the sensor when the sensor is replaced after having been removed. Certain metrics, which may be referred to as "quality metrics" may be calculated from sensor measurements; these quality metrics may be indications of the expected performance of the sensor, e.g., its ability to detect, or measure the concentration of, certain constituents of the tissue being analyzed. Such quality metrics may be analyzed, and communicated to the user (e.g., using audible, graphical, or haptic feedback, as discussed above) to help the user place the sensor at a position on the subject at which it will perform well, or, if the sensor was previously placed on the subject at such a position and then removed, to return it to such a position. Such metrics may also confirm successful repositioning of the sensor when used in combination with a mechanical repositioning setup (e.g., a holder, as discussed above), or to monitor the signal quality and provide feedback to the user regarding any need to adjust the sensor (e.g., to relocate or replace the sensor, or to make a tension adjustment in a mechanical attachment such as a strap).

Two general classes of signals that may be analyzed for quality metrics in order to facilitate positioning or repositioning of the sensor include (i) time varying signals e.g., photoplethysmography (PPG) (either absorbance based or speckle based), and (ii) time invariant signals of absorbance that may be expected to follow a known wavelength dependent behavior (e.g., water or collagen absorbance in the short wavelength infrared (SWIR) region of the optical spectrum, or melanin absorbance in the visible region of the optical spectrum).

For example, the sensor may include a photoplethysmography sensor (e.g., in addition to a spectrophotometer). Time varying signals related to blood flow, for example, may then be used to detect, for example, pulse rate and variability, respiration rate, blood pressure, blood diffusion, blood perfusion, and blood oxygenation. Factors affecting the quality of the signals may include the physical location of the sensor relative to underlying blood vessels, the tension in a strap (such as a watch band) securing the sensor to the subject, and any interfering substances or materials at the skin/optics interface. Quality metrics, for such a sensor, may include the peak-to-peak amplitude of the AC signal, the ratio of the AC signal to the DC signal, the frequency content of the signal (as determined, e.g., by Fast Fourier Transform (FFT) of the signal), from which the signal to noise ratio may be estimated, and rise time or fall time of pulse edges of the signal. If the sensor used to measure time varying signals measures at multiple wavelengths, then the AC signal may be wavelength dependent and the signals corresponding to different wavelengths may be combined (e.g., a weighted average of the peak-to-peak amplitudes may be calculated) to form a quality metric. Time varying signals may also be used to find sensor positions suitable for spectrophotometric measurements. For example, the peak-to-peak amplitude of a time-varying signal may be an indication of perfusion, which in turn may be correlated with signal quality in the spectrophotometer.

The chemical composition of the tissue of the subject may be relatively well known a priori, and this knowledge may be used to calculate a quality metric, e.g., an indicator of the quality of the interface between the sensor and the tissue. For example, the tissue may be expected to contain water, collagen, and lipids, each within a respective known range. Discrepancies between the measured concentrations of such constituents and the expected concentrations may therefore be an indication of poor sensor positioning (e.g., sensor positioning that allows excessive stray light to reach the receiver). If a sensor is being repositioned after having been removed, the measurements may be compared directly to a previously stored, good measurement of the subject, thereby providing sensitive feedback on the repeatability of the positioning of the sensor.

For example, water absorbance curve fitting may be used to detect stray light caused by inadequate skin contact or by a poor location of the sensor on the body of the subject. As another example, the peak-to-trough absorbance change across wavelength range being tested may be used as a quality metric suitable for real-time monitoring of interface quality on edge devices (e.g., devices with relatively low processing power, such as smart watches).

In some embodiments, a stored library of samples for the sensor may be compiled into a set of loading vectors. Each such loading vector may be a vector (e.g., a vector of spectral samples) in an N-dimensional measurement space (e.g., the space of multispectral measurements performed with N wavelengths). If M such loading vectors are used (with, e.g., M being less than N) then each new measurement may be converted from an N-dimensional vector to an M-dimensional vector by projection onto each of the loading vectors in turn. Each such M-dimensional vector may consist of (e.g., its elements may be) the scalar projections of a vector of spectral samples onto the loading vectors, each scalar projection being equal to the dot product of the vector of spectral samples and a loading vector, divided by the magnitude of the loading vector. Distance metrics (e.g., the Mahalanobis distance or Euclidean distance) may then be used to calculate the distances between the M-dimensional vectors, and to quantify the similarity of the sample under test to the samples in the library.

In some embodiments, repositioning of a sensor after it has been removed, or assessment of how well a mechanical holder 100 (e.g., as described above) has caused the sensor to be returned to a previously used position, may be performed using one or more repeatability metrics. Such metrics may measure how nearly a new sensor position is the same as a previously used sensor position. To use a direct comparison to a previously stored measurement, a known good measurement of the user may be stored and compared to subsequent measurements, e.g., by subtracting the prior measurement from the new measurement. An appropriate pre-treatment, or "correction" may be applied to the new measurement and to the previously stored measurement (e.g. conversion to optical absorbance) prior to performing this subtraction. Examples of spectral corrections which may be applied prior to comparison include but are not limited to: sensor wavelength correction, optical power correction, linear baseline removal, and first or second derivative processing. Examples of repeatability metrics that may be calculated from such corrected signals include (i) peak-to-trough absorbance change across wavelength range (e.g., the difference between (a) a maximum reading, over wavelength, obtained by the spectrophotometer, and (b) a minimum reading, over wavelength, obtained by the spectrophotometer), and (ii) multivariate distance calculations. To use multivariate distance calculations, for example, the new measurement and a previously obtained measurement may each be projected onto a set of M loading vectors, and distance metrics (e.g., the Mahalanobis distance or Euclidean distance) may then be used to calculate the distances between the M-dimensional vectors, and to determine similarity of the new sensor position to the previous sensor position. Residual testing may be used to assess whether the projection onto the loading vectors is producing reliable results. The residual information content (e.g., the magnitude of the difference between (i) each N-dimensional vector and (ii) the sum of its projections onto the loading vectors)

after projection into the stored loading vectors may be calculated. Significant residual information content may indicate the presence of unexpected signals indicating imperfect positioning of the sensor.

Although examples are described herein in the context of a sensor that is a spectrophotometer, the present disclosure is not limited to such embodiments, and methods disclosed herein may be used to position, or reposition, other types of instruments on a subject. Similar approaches may also be used when testing in vitro aqueous samples. For example, a low calculated value for a quality metric may be an indication of inadequate sample volume or incorrect insertion of a test cartridge.

As used herein, "a portion of" something means "at least some of" the thing, and as such may mean less than all of, or all of, the thing. As such, "a portion of" a thing includes the entire thing as a special case, i.e., the entire thing is an example of a portion of the thing. As used herein, when a second quantity is "within Y" of a first quantity X, it means that the second quantity is at least X−Y and the second quantity is at most X+Y. As used herein, when a second number is "within Y %" of a first number, it means that the second number is at least (1−Y/100) times the first number and the second number is at most (1+Y/100) times the first number. As used herein, the word "or" is inclusive, so that, for example, "A or B" means any one of (i) A, (ii) B, and (iii) A and B.

As used herein, when a method (e.g., an adjustment) or a first quantity (e.g., a first variable) is referred to as being "based on" a second quantity (e.g., a second variable) it means that the second quantity is an input to the method or influences the first quantity, e.g., the second quantity may be an input (e.g., the only input, or one of several inputs) to a function that calculates the first quantity, or the first quantity may be equal to the second quantity, or the first quantity may be the same as (e.g., stored at the same location or locations in memory as) the second quantity.

The terminology used herein is for the purpose of describing particular embodiments only and is not intended to be limiting of the inventive concept. As used herein, the terms "substantially," "about," and similar terms are used as terms of approximation and not as terms of degree, and are intended to account for the inherent deviations in measured or calculated values that would be recognized by those of ordinary skill in the art.

Any numerical range recited herein is intended to include all sub-ranges of the same numerical precision subsumed within the recited range. For example, a range of "1.0 to 10.0" or "between 1.0 and 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Similarly, a range described as "within 35% of 10" is intended to include all subranges between (and including) the recited minimum value of 6.5 (i.e., (1−35/100) times 10) and the recited maximum value of 13.5 (i.e., (1+35/100) times 10), that is, having a minimum value equal to or greater than 6.5 and a maximum value equal to or less than 13.5, such as, for example, 7.4 to 10.6. Any maximum numerical limitation recited herein is intended to include all lower numerical limitations subsumed therein and any minimum numerical limitation recited in this specification is intended to include all higher numerical limitations subsumed therein.

Although exemplary embodiments of a system and method for positioning a sensor on a subject have been specifically described and illustrated herein, many modifications and variations will be apparent to those skilled in the art. Accordingly, it is to be understood that a system and method for positioning a sensor on a subject constructed according to principles of this disclosure may be embodied other than as specifically described herein. The invention is also defined in the following claims, and equivalents thereof.

What is claimed is:

1. A system, comprising:
   a sensor module comprising at least one of a spectrophotometer or a photoplethysmography sensor;
   a cap having a porous top; and
   an instrument holder configured to temporarily hold each of the sensor module and the cap, and comprising:
      a flexible fabric portion configured to be secured to a subject by an adhesive, and
      a rigid portion secured to the flexible fabric portion and comprising a socket defining an aperture, the socket comprising:
         a flat base secured to the flexible fabric portion;
         a plurality of straight walls that extend away from the flat base and that surround the aperture and form a plurality of internal corners of the aperture; and
         a detent comprising a plurality of rounded ribs or rounded recesses in the plurality of straight walls, the plurality of rounded ribs or rounded recesses being configured to hold the sensor module by engaging, via a snap fit, a corresponding plurality of rounded recesses or rounded ribs of the sensor module, and to hold the cap by engaging, via a snap fit, a corresponding plurality of rounded recesses or rounded ribs of the cap,
   wherein each of the plurality of rounded ribs or rounded recesses in the plurality of straight walls is spaced apart, along the plurality of straight walls, from both the flat base and a distal edge of the corresponding straight wall of the plurality of straight walls, the distal edge being distal to the flat base,
   wherein a horizontal cross section of the sensor module and a horizontal cross section of the aperture match,
   wherein the instrument holder is configured so that the sensor module contacts the skin of the subject when installed in the instrument holder, and
   wherein the instrument holder is configured such that, when the sensor module is held by the instrument holder, a maximum distance by which any portion of the sensor module is movable, relative to the instrument holder, in both translational directions along each of three orthogonal axes is 1 mm or less, and a maximum extent to which any portion of the sensor module is rotatable, relative to the instrument holder, in both rotational directions about each of the three orthogonal axes is 2.5 degrees or less.

2. The system of claim 1, wherein the sensor module comprises at least the spectrophotometer.

3. The system of claim 2, wherein the sensor module further comprises the photoplethysmography sensor.

4. A method for positioning the sensor module using the system of claim 1, the method comprising:
   holding, by the instrument holder, the sensor module on a first occasion;
   removing the sensor module from the instrument holder after the first occasion;
   holding, by the instrument holder, the sensor module on a second occasion after the removing the sensor module from the instrument holder; and calculating a repeatability metric based on a measurement obtained by the sensor module on the first occasion and a measurement obtained by the sensor module on the second occasion.

5. The method of claim 4, wherein the calculating of the repeatability metric comprises calculating a difference between a peak-to-trough measurement obtained on the first occasion and a peak-to-trough measurement obtained on the second occasion, each of the peak-to-trough measurements being a difference between a maximum measured value and a minimum measured value.

6. The method of claim 5, wherein:

the sensor module comprises the spectrophotometer, and the peak-to-trough measurement obtained on the first occasion is the difference between:

a maximum reading, over wavelength, obtained by the spectrophotometer, and a minimum reading, over wavelength, obtained by the spectrophotometer.

7. The method of claim 4, wherein:

the sensor module comprises the spectrophotometer;

the measurement obtained by the sensor module on the first occasion comprises a first vector of spectral samples;

the measurement obtained by the sensor module on the second occasion comprises a second vector of spectral samples;

the calculating of the repeatability metric comprises calculating a distance between a first vector of scalar projections and a second vector of scalar projections;

each element of the first vector of scalar projections is a scalar projection of the first vector of spectral samples onto a corresponding loading vector of a plurality of loading vectors; and each element of the second vector of scalar projections is a scalar projection of the second vector of spectral samples onto a corresponding loading vector of the plurality of loading vectors.

8. The method of claim 7, wherein the distance is a Mahalanobis distance.

9. The method of claim 7, wherein the distance is a Euclidean distance.

* * * * *